United States Patent [19]

Jackson

[11] Patent Number: 5,650,521
[45] Date of Patent: Jul. 22, 1997

[54] PYRROLIDINE DERIVATIVES

[75] Inventor: Paul F. Jackson, Bel Air, Md.

[73] Assignee: Guilford Pharmaceuticals Inc., Baltimore, Md.

[21] Appl. No.: 580,607

[22] Filed: Dec. 29, 1995

[51] Int. Cl.$^6$ .................... C07D 207/08; A01N 43/36; A61K 31/40
[52] U.S. Cl. ............................... 548/556; 548/570
[58] Field of Search .................... 548/556, 570; 514/429, 428

[56] References Cited

U.S. PATENT DOCUMENTS

| | | |
|---|---|---|
| 4,762,843 | 8/1988 | Caprathe et al. . |
| 5,039,802 | 8/1991 | Blacklock et al. . |
| 5,180,729 | 1/1993 | Cook . |
| 5,262,428 | 11/1993 | Davies et al. . |
| 5,268,480 | 12/1993 | Kozikowski . |
| 5,298,509 | 3/1994 | Schuster et al. . |

FOREIGN PATENT DOCUMENTS

4341605A1  8/1995  Germany .

OTHER PUBLICATIONS

"Catalytic Asymmetric Induction, Highly Enantioselective Addition of Dialkylzincs to Aldehydes Using Chiral Pyrrolidinylmethanols and Their Metal Salts," Soai et al., *J. Am. Chem. Soc.* 1987, 109, 7111–7115.

*Primary Examiner*—Johann Richter
*Assistant Examiner*—Jane C. Oswecki
*Attorney, Agent, or Firm*—Nath & Associates; Gary M. Nath; Suet M. Chong

[57] ABSTRACT

The invention relates to pyrrolidine derivatives and pharmaceutically acceptable salts thereof, pharmaceutical compositions comprising the same, and methods of treating cocaine addiction and overdose, and diseases and conditions characterized by abnormal dopaminergic neurotransmission, with pyrrolidine derivatives.

17 Claims, No Drawings

PYRROLIDINE DERIVATIVES

BACKGROUND OF THE INVENTION

Dopamine is a catecholamine which is one of the principal neurotransmitters present in the central nervous system. Abnormalities in dopaminergic neurotransmission have been implicated in a variety of disease states including Parkinson's disease, depression, attention deficit disorder, and drug addiction.

The major pathway by which monoamines are inactivated is by being transported back into the cell that released them via specific transporter proteins (i.e. serotonin, norepinephrine, and dopamine transporter proteins). The dopamine transporter protein is the carrier molecule which transports dopamine across the synaptic membrane (Hitri et al., Clinical Neuropharmacology, 1994, 17, 1–22). The human dopamine transporter protein was recently cloned, and shown to have several binding sites, including a binding site for cocaine (Giros et al., Mol. Pharmacol., 1992, 42, 383–390).

Major depression, which is characterized by feelings of intense sadness or pessimistic worry, affects approximately 5–10% of the population (Michels, (ed.) Psychiatry Philadelphia: Lipincott, 1992). A variety of medications have shown efficacy in treating depression including the tricyclic antidepressants, serotonin uptake inhibitors, and monoamine oxidase inhibitors (Pinder et al., Med. Res. Rev., 1993, 13, 259–325). All of these compounds work by increasing the synaptic levels of monoamine neurotransmitters. There are several reports in the literature of selective dopamine uptake inhibitors showing efficacy in animal models of depression (Nielsen et al., Adv. Biosci., 1990, 77, 101–108; Randrup et al., Psychopharmacology, 1977, 52, 73–77; Halaris et al., Biochem. Pharmacol., 1975, 24, 1896–1897).

Parkinson's disease is a progressive, degenerative neurologic motor disorder produced by the loss of dopaminergic neurons in the substantia nigra. This in turn results in abnormally low levels of dopamine present in the striatum. As a result, drugs that can increase the levels of dopamine have the potential to be useful in the treatment of Parkinson's Disease. The most widely prescribed drug in this class is the dopamine precursor levodopa (L-DOPA) (McDowell et al., Ann. Intern. Med., 1970, 72, 29–35). Another mechanism to increase levels of synaptic dopamine is to block its reuptake via inhibition of the dopamine transporter protein. There have been several studies demonstrating that compounds which act by inhibiting the action of the dopamine transporter protein are effective in animal models of Parkinson's Disease (Mayer et al., MPTP: Neurotoxin Prod. Parkinsonian Syndr., Markey et al., ed., 1985, 585–589). For example, the selective dopamine uptake inhibitor GBR 13,098 is effective at preventing MPTP induced toxicity in mice (Pileblad et al., Neuropharmacology, 1985, 24, 689–692).

Attention deficit disorder (ADD) manifests itself primarily in children. The symptoms include an inability to remain focused on a particular task for an extended period of time (Funk et al., Pediatrics, 1993, 91, 816–819). A variety of drugs have been prescribed for this disease, including dextroamphetamine and methylphenidate. Methylphenidate appears to exert its effects by inhibiting the dopamine transporter, more specifically by binding to the cocaine site on the dopamine transporter (Volkow et al., Arch. Gen. Psychiatry, 1995, 52, 456–63). As a result, compounds which have a similar mode of action at this binding site may also show efficacy in this disease.

Cocaine addiction affects approximately 2.1 million people in the United States (Committee to Study Medication Development and Research at the National Institute on Drug Abuse, "Extent of Illicit Drug Use", *Development of Medications for the Treatment of Opiate and Cocaine Additions: Issues for the Government and Private Sector*, Fulco, Liverman, Earley, Eds., National Academy Press, Washington, D.C., 1995, 36–37). In the last decade the molecular site of cocaine's addictive properties has been determined to be the dopamine transporter protein (Kuhar et al., TIPS, 1991, 14, 299–302). It was originally proposed that cocaine was a competitive inhibitor of dopamine uptake, coincident with cocaine and dopamine having common binding domains on the transporter protein. However, recent evidence suggest that dopamine and cocaine binding sites on the DAT are distinct (Kityama et al., Proc. Natl. Acad. Sci. USA, 1992, 89, 7782–7785).

Partial agonists and/or antagonists at the cocaine site on the dopamine transporter protein may show efficacy in treating cocaine addiction. Importantly, several compounds which bind to the cocaine binding site have been shown to block the effects of cocaine in vivo. For example, GBR 12909 has been shown to attenuate cocaine-induced activation of mesolimbic dopamine neurons in rat (Baumann et al., J. Pharm. Exp. Therap., 1994, 271, 1216–1222). Compounds which bind to the cocaine site but do not inhibit dopamine uptake (i.e. a cocaine antagonist) may have utility in the treatment of cocaine addiction (Carroll, FI et al., Pharmaceutical News, 1994, 1, 11–17).

There are currently no medications which effectively treat cocaine addiction. Accordingly, a need exists for compounds having an affinity for the cocaine site on a dopamine transporter protein (DAT), without inhibiting dopamine uptake, to aid in the treatment of cocaine addiction.

A further need exists for compounds which inhibit dopamine uptake to aid in the treatment of neurological disorders characterized by abnormal dopaminergic neurotransmission, notably Parkinson's disease, depression, and attention deficit disorder (ADD).

The applicant has discovered new compounds that are useful for the above described treatments, as well as new methods of using known compounds that are related in structure to the new compounds.

SUMMARY OF THE INVENTION

The present invention relates to a compound of the formula

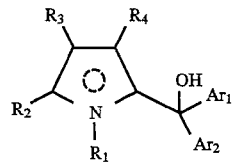

or a pharmaceutically acceptable salt thereof, wherein the compound is an R- or S-enantiomer;

the pyrrolidine ring is saturated or unsaturated;

$R_1$, $R_2$, $R_3$ and $R_4$ are independently selected from the group consisting of H, $C_1$–$C_6$ alkyl, hydroxy, carboxy, alkoxy and substituted $C_1$–$C_6$ alkyl group;

$R_1$, $R_2$, $R_3$ and $R_4$ are not all H; and $Ar_1$ and $Ar_2$ are independently selected from the group consisting of an unsubstituted phenyl radical, a monosubstituted phenyl radical, and a multisubstituted phenyl radical, with substituents selected from the group consisting of halogen, $C_1$–$C_6$ alkyl, substituted alkyl, hydroxy, alkoxy, and carboxy.

The present invention also relates to a compound of the formula

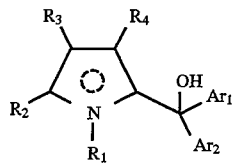

I or a pharmaceutically acceptable salt thereof, wherein the compound is an R- or S-enantiomer;

the pyrrolidine ring is saturated or unsaturated;

$R_1$, $R_2$, $R_3$ and $R_4$ are independently selected from the group consisting of H, $C_1$–$C_6$ alkyl, hydroxy, carboxy, alkoxy and substituted $C_1$–$C_6$ alkyl group; and $Ar_1$ and $Ar_2$ are independently a phenyl radical substituted with a fluorine, bromine or iodine, and at least one other substituent selected from the group consisting of a halogen, $C_1$–$C_6$ alkyl, substituted alkyl, hydroxy, alkoxy, and carboxy.

The present invention further relates to a pharmaceutical composition comprising:

(a) a therapeutically effective amount of a compound of formula

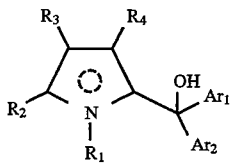

I or a pharmaceutically acceptable salt thereof, wherein the compound is an R- or S-enantiomer;

the pyrrolidine ring is saturated or unsaturated;

$R_1$, $R_2$, $R_3$ and $R_4$ are independently selected from the group consisting of H, $C_1$–$C_6$ alkyl, hydroxy, carboxy, alkoxy and substituted $C_1$–$C_6$ alkyl group;

$R_1$, $R_2$, $R_3$ and $R_4$ are not all H; and $Ar_1$ and $Ar_2$ are independently selected from the group consisting of an unsubstituted phenyl radical, a monosubstituted phenyl radical, and a multisubstituted phenyl radical, with substituents selected from the group consisting of halogen, $C_1$–$C_6$ alkyl, substituted alkyl, hydroxy, alkoxy, and carboxy; and (b) at least one of a pharmaceutically acceptable carrier, excipient or diluent.

The present invention also relates to a method of treating a disease state or condition characterized by abnormal dopaminergic neurotransmission, which comprises administering to a host suffering therefrom a therapeutically effective amount of a compound having the formula

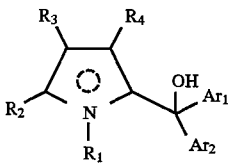

I or a pharmaceutically acceptable salt thereof, wherein the compound is an R- or S-enantiomer;

the pyrrolidine ring is saturated or unsaturated;

$R_1$, $R_2$, $R_3$ and $R_4$ are independently selected from the group consisting of H, $C_1$–$C_6$ alkyl, hydroxy, carboxy, alkoxy and substituted $C_1$–$C_6$ alkyl group; and $Ar_1$ and $Ar_2$ are independently selected from the group consisting of an unsubstituted phenyl radical, a monosubstituted phenyl radical, and a multisubstituted phenyl radical, with substituents selected from the group consisting of halogen, $C_1$–$C_6$ alkyl, substituted alkyl, hydroxy, alkoxy, and carboxy.

The present invention further relates to a method of treating cocaine addition or overdose, which comprises administering to a host suffering therefrom a therapeutically effective amount of a compound having the formula

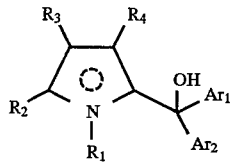

I or a pharmaceutically acceptable salt thereof, wherein the compound is an R- or S-enantiomer;

the pyrrolidine ring is saturated or unsaturated;

$R_1$, $R_2$, $R_3$ and $R_4$ are independently selected from the group consisting of H, $C_1$–$C_6$ alkyl, hydroxy, carboxy, alkoxy and substituted $C_1$–$C_6$ alkyl group; and $Ar_1$ and $Ar_2$ are independently selected from the group consisting of an unsubstituted phenyl radical, a monosubstituted phenyl radical, and a multisubstituted phenyl radical, with substituents selected from the group consisting of halogen, $C_1$–$C_6$ alkyl, substituted alkyl, hydroxy, alkoxy, and carboxy.

DETAILED DESCRIPTION OF THE INVENTION

DEFINITIONS

"Alkyl" means a branched or unbranched saturated hydrocarbon chain containing 1 to 6 carbon atoms, such as methyl, ethyl, propyl, iso-propyl, butyl, iso-butyl, tert-butyl, n-pentyl, n-hexyl, and the like, unless otherwise indicated.

"Alkoxy" means the group —OR wherein R is alkyl as herein defined. Preferably, R is a branched or unbranched saturated hydrocarbon chain containing 1 to 3 carbon atoms.

"Halo" means fluoro, chloro, bromo, or iodo, unless otherwise indicated.

"Phenyl" includes all possible isomeric phenyl radicals, optionally monosubstituted or multi-substituted with substituents selected from the group consisting of alkyl, alkoxy, hydroxy, halo, and haloalkyl.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and substituted phenyl.

The term "pharmaceutically acceptable salt" refers to salts of the subject compounds which possess the desired pharmacological activity and which are neither biologically nor otherwise undesirable. The salts can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The compounds of this invention possess asymmetric centers and thus can be produced as mixtures of stereoisomers or as individual stereoisomers. The individual stereoisomers may be obtained by using an optically active starting material, by resolving a racemic or non-racemic mixture of an intermediate at some appropriate stage of the synthesis, or by resolution of the compound of formula (I). It is understood that the individual stereoisomers as well as mixtures (racemic and non-racemic) of stereoisomers are encompassed by the scope of the present invention. The compounds of this invention possess at least two asymmetric centers and thus can be produced as mixtures of stereoisomers or as individual R- and S-stereoisomers. The individual enantiomers may be obtained by resolving a racemic or non-racemic mixture of an intermediate at some appropriate stage of the synthesis. It is understood that the individual R- and S- stereoisomers as well as mixtures of stereoisomers are encompassed by this invention. The R-stereoisomer is most preferred due to its greater activity.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other.

"Diastereoisomers" are stereoisomers which are not mirror images of each other.

"Racemic mixture" means a mixture containing equal parts of individual enantiomers. "Non-racemic mixture" is a mixture containing unequal parts of individual enantiomers or stereoisomers.

The term "treatment" as used herein covers any treatment of a disease and/or condition in a mammal, particularly a human, and includes:

(i) preventing a disease and/or condition from occurring in a subject which may be predisposed to the disease and/or condition but has not yet been diagnosed as having (ii) inhibiting the disease and/or condition, i.e., arresting its development; or (iii) relieving the disease and/or condition, i.e., causing regression of the disease and/or condition.

The system used in naming the intermediates and product compounds of the present invention is shown below, using a compound of formula (I) wherein each $R_1$ and $R_2$ is hydrogen and X is —$(CH_2)_7$— is named:

The system used in naming the compounds of the present invention is shown below, using a compound of formula I as an example.

A compound of formula I wherein $R_1$, $Ar_1$ and $Ar_2$ are H is named diphenyl-2-pyrrolidine-methanol.

As used in this specification and the appended claims, the singular forms "a", "an" and "the" include plural reference unless the context clearly dictates otherwise. Thus, for example, reference to a pyrrolidine derivative includes mixtures of such compounds and so forth.

Compounds of the Invention

The present invention relates to compounds of the formula

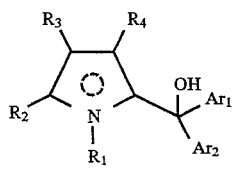

I wherein the compound is an R- or S-enantiomer;

the pyrrolidine ring is saturated or unsaturated;

$R_1$, $R_2$, $R_3$ and $R_4$ are independently selected from the group consisting of H, $C_1$–$C_6$ alkyl, hydroxy, carboxy, alkoxy and substituted $C_1$–$C_6$ alkyl group;

$R_1$, $R_2$, $R_3$ and $R_4$ are not all H; and $Ar_1$ and $Ar_2$ are independently selected from the group consisting of an unsubstituted phenyl radical, a monosubstituted phenyl radical, and a multisubstituted phenyl radical, with substituents selected from the group consisting of halogen, $C_1$–$C_6$ alkyl, substituted alkyl, hydroxy, alkoxy, and carboxy.

The compounds of the present invention exist as stereoisomeric forms, either enantiomers or diastereoisomers. Included within the scope of the invention are the enantiomers, the racemic form, and diastereoisomeric mixtures. Enantiomers and diastereoisomers can be separated by methods known to those skilled in the art.

In a preferred embodiment, $R_1$ is selected from the group consisting of methyl, ethyl, propyl, butyl. In another preferred embodiment, $Ar_1$ is selected from the group consisting of 4-fluorophenyl, 4-chlorophenyl, and 3-methyl-4-fluorophenyl. In a further preferred embodiment, $Ar_2$ is selected from the group consisting of 4-fluorophenyl, 4-chlorophenyl, and 3-methyl-4-fluorophenyl.

The most preferred compounds of the present invention are:

(S)-(−)-1-methyl-α,α-diphenyl-2-pyrrolidinemethanol;
(R)-(+)-1-methyl-α,α-diphenyl-2-pyrrolidinemethanol;
(S)-(−)-1-ethyl-α,α-diphenyl-2-pyrrolidinemethanol;
(R)-(+)-1-ethyl-α,α-diphenyl-2-pyrrolidinemethanol;
(S)-(−)-1-propyl-α,α-diphenyl-2-pyrrolidinemethanol;
(R)-(+)-1-propyl-α,α-diphenyl-2-pyrrolidinemethanol;
(S)-(−)-1-butyl-α,α-diphenyl-2-pyrrolidinemethanol; and
(R)-(+)-1-butyl-α,α-diphenyl-2-pyrrolidinemethanol.

The present invention also relates to a compound of the formula

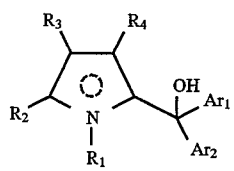

or a pharmaceutically acceptable salt thereof, wherein
the compound is an R- or S-enantiomer;
the pyrrolidine ring is saturated or unsaturated;
$R_1$, $R_2$, $R_3$ and $R_4$ are independently selected from the group consisting of H, $C_1$–$C_6$ alkyl, hydroxy, carboxy, alkoxy and substituted $C_1$–$C_6$ alkyl group; and
$Ar_1$ and $Ar_2$ are independently a phenyl radical substituted with a fluorine, bromine or iodine, and at least one other substituent selected from the group consisting of $C_1$–$C_6$ alkyl, substituted alkyl, hydroxy, alkoxy, and carboxy.

In a preferred embodiment, the compound of formula I is (S)-α,α-Bis(3-methyl-4-fluorophenyl)-2-pyrrolidinemethanol.

METHODS OF PREPARATION

Some of the compounds of formula I are known or capable of being prepared by those skilled in the art using methods known in the art. Thus, for example, (S)-α,α-Diphenyl-2-pyrrolidinemethanol is a known compound and has been prepared by a variety of processes known in the art. See, for example, German Patent DE 43 41 605 A1; and U.S. Pat. No. 5,039,802.

Preferably, the compounds of formula I are prepared according to Scheme 1:

Scheme 1

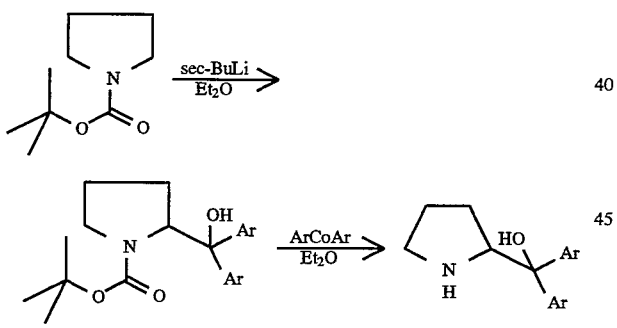

This route has been described by Mahre et al., J. Org. Chem., 1991, 56, 751–762.

By using either D-, or L-proline as the starting material, the final product can be obtained as either the pure R or pure S-enantiomer.

More preferably, the compounds of formula I are prepared according to Scheme 2.

Scheme 2

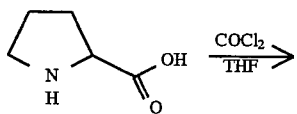

-continued
Scheme 2

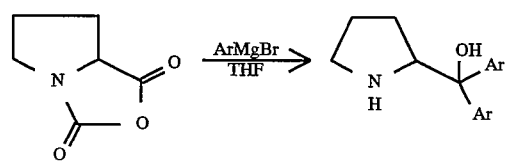

This route has been described by Kerrick et al., J. Am. Chem. Soc., 1991, 113, 9708–9710.

Again, either enantiomer of the final product can be obtained by adding either (+) or (−)-sparteine to the first step.

Substitutions of the pyrrolidine ring or the aryl groups can be achieved by any process known in the art.

EXAMPLES

The following examples are illustrative of the present invention and are not intended to be limitations thereon. All percentages are based on 100% by weight of the final compound.

Example 1

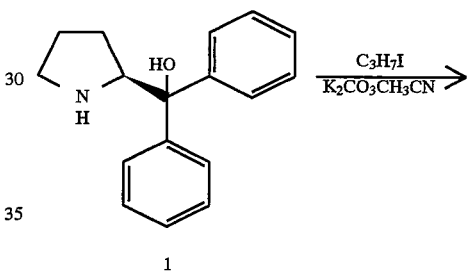

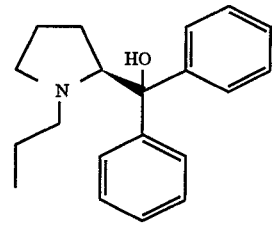

2

(S)-(−)-1-propyl-α,α-diphenyl-2-pyrrolidinemethanol (Compound 2)

(S)-(−)-α,α-diphenyl-2-pyrrolidinemethanol (1) (1.0 g, 4.0 mmol) was added to a flask containing potassium carbonate (1.2 g, 8.7 mmol) and 20 ml of acetonitrile. Propyl iodide (2.0 ml, 21 mmol) was added and the resulting mixture heated to reflux for three hours. At the end of this time, the mixture was cooled to room temperature, added to brine (50 ml), and extracted with ethyl acetate. The ethyl acetate layer was washed once with brine, dried over anhydrous magnesium sulfate, and the solvent removed under reduced pressure. This afforded the desired material (2) (0.98 g, 84%) as a white solid.

1H NMR (DMSO-d6) 0.5 (t, 3H), 1.0–1.2 (m, 2H), 1.3–1.9 (m, 5H), 2.0–2.1 (m, 1H), 2.3 (q, 1H), 3.1 (m, 1H), 3.9 (m, 1H), 5.1 (br s, 1H), 7.0–7.3 (m, 6H), 7.5–7.7 (m, 4H)

Example 2

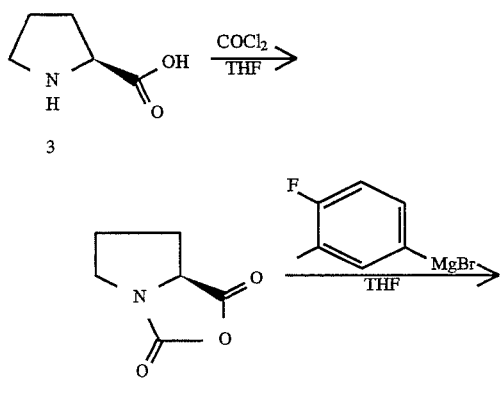

3

4

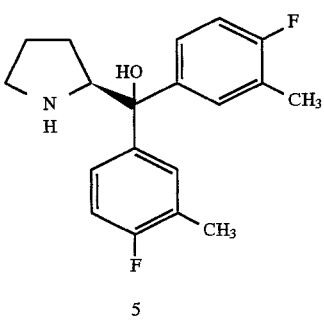

5

(S)-α,α-Bis(3-methyl-4-fluorophenyl)-2-pyrrolidinemethanol (Compound 5)

4-Fluoro-3-methylphenylmagnesium bromide (16.0 ml, 1.0M in tetrahydrofuran, 32 mmol) was added to a 500 ml three neck round bottom flask containing a low temperature thermometer and a 50 ml dropping funnel. This was then cooled to −15° C. under an atmosphere of nitrogen. (S)-Tetrahydro- 1H,3H-pyrrolo[1,2-c]oxazole-1,3-dione (4) (1.50 g, 10.6 mmol) in dry tetrahydrofuran (10 ml) was added to the dropping funnel. This solution was then added dropwise to the Grignard reagent at such a rate as to maintain the reaction temperature between −15° C. and −10° C. The addition was complete in approximately 45 minutes. The mixture was stirred for 2 hours at −15° C. and 1 hour at 0° C. before being poured into a precooled (0° C) solution of sulfuric acid (25 ml, 2.0M). After 5 minutes a thick white precipitate formed. The mixture was cooled for an additional 1 hour, filtered, and washed twice with THF(150 ml). The resulting solution was then concentrated to a volume of 50 ml. This was then cooled to 0° C. and a yellow precipitate formed. After 30 minutes, the precipitate was filtered, washed twice with 20 ml of water and twice with 50 ml of ethyl acetate. The desired material as its sulfate salt was obtained as a white solid (2.0 g, 52%). A portion of the salt (0.50 g, 0.70 mmol) was added to a 1.0M potassium hydroxide solution (10 ml) and stirred at room temperature for 1 hour. At the end of this time, toluene (25 ml) was added and the mixture filtered. The aqueous layer was removed and the organic phase was washed once with water (25 ml). This was then dried with anhydrous magnesium sulfate and evaporated under reduced pressure to give the desired product (5) (0.37 g, 84%) as a clear and colorless oil.

$^1$H NMR (DMSO d$_6$) δ1.6–2.2 (m, 4H), 2.1 (s, 6H), 2.3 (s, 1H), 2.8 (m, 2H), 4.15 (t, 1H), 5.1 (s, 1H), 6.9–7.0 (appt, 2H), 7.1–7.5 (m, 4H).

Example 3

(S)-Tetrahydro-1H,3H-pyrrolo[1,2-c]oxazole-1,3-dione (Compound 4)

L-Proline (11.5 g, 0.10 mol) was added to a 500 ml three neck flask fitted with a 125 ml addition funnel, thermometer and a nitrogen inlet tube. To the flask was added dry tetrahydrofuran (115 ml) and the mixture cooled to 15° C. using an ice/water bath. The addition funnel was charged with diphosgene (7.2 ml, 0.06 mol) and dry THF(50 ml). The diphosgene solution was added dropwise to the proline mixture over 45 minutes while maintaining a reaction mixture temperature in the range of 15° to 20° C. Once the addition was complete the mixture was warmed to 35° C. for 1 hour. At the end of this time a clear and colorless solution was obtained. The reaction mixture was then cooled to room temperature and concentrated under vacuum to a volume of approximately 50 ml. The residue was redissolved in 115 ml of THF and cooled to 0°–5° C. using an ice bath. Triethylamine (12 ml, 0.086 mol) was added dropwise to the cooled solution over 30 minutes. The solution was stirred a further 30 minutes after which time the solids were filtered and washed with THF(100 ml). The organics were concentrated under reduced pressure to give the desired compound (4) (14 g, 99%) as a light beige solid. The material was stored under nitrogen at −78° C. in order to avoid decomposition, and used without further purification in subsequent reactions.

PHARMACOLOGICAL ACTIVITY

Four compounds of formula I were tested in vitro for their ability to displace the cocaine analogue (−)-2-β-[$^3$H] carbomethoxy-3β-(4-fluorophenyl)tropane binding at the cocaine site on the dopamine transporter protein (DAT) (expressed as Ki$_{binding}$), and for their ability to block dopamine uptake into neurons by inhibiting the neuronal dopamine transporter (expressed as Ki$_{uptake}$).

The following Table I compares the Ki$_{binding}$ and Ki$_{uptake}$ values and the uptake to binding ratios (Ki$_{uptake}$/Ki$_{binding}$ of the tested compounds with those of cocaine.

TABLE I

Pharmacological Activity of Compounds of Formula I

| Compound | Affinity to the Cocaine Binding Site ($Ki_{binding}$) | Effect on Dopamine Uptake ($Ki_{uptake}$) | Uptake to Binding Ratio ($Ki_{uptake}/Ki_{binding}$) |
|---|---|---|---|
| Cocaine | 0.12 μM | 0.20 μM | 1.67 |
| (R)-(+)-α,α-diphenyl-2-pyrrolidinemethanol | 0.04 | 0.17 | 4.25 |
| (S)-(−)-α,α-diphenyl-2-pyrrolidinemethanol | 0.40 | 1.65 | 4.12 |
| (S)-(−)-1-propyl-α,α-diphenyl-2-pyrrolidine-methanol | 3.30 | 10.3 | 3.12 |
| (S)-α,α-Bis(3-methyl-4-fluorophenyl)-2-pyrrolidine-methanol | 0.26 | 0.44 | 1.69 |

$Ki_{binding}$ represents the potency of cocaine (a cocaine analogue is used in place of cocaine in the test procedures because cocaine itself is unstable) in binding to the dopamine transporter protein (DAT). Thus, the lower the $Ki_{binding}$ values means the greater the ability of the tested compounds to antagonize cocaine's binding to the DAT.

$Ki_{uptake}$ represents the levels of dopamine uptake. The higher the $Ki_{uptake}$ values means the higher the selectivity of the tested compounds in binding to the cocaine site on the DAT and, thus, the lower the inhibition of the functioning of the DAT.

Based on the data in Table I, cocaine is nonselective with an uptake to binding ratio of 1.7. All the tested compounds of formula I exhibit uptake to binding ratios greater than that of cocaine, which mean that the compounds bind potently to the cocaine site on the DAT and have little or no effect on dopamine uptake.

Test Procedures

Values (Ki values) for the binding of compounds at the cocaine binding site of the human dopamine transporter as well as values for the inhibition of dopamine uptake can be obtained using methods described in the literature (Kitayama, S., Shimada, S., Xu, H., Markham, L., Donovan, D. M., and Uhl, G. R. (1992) Proc. Natl. Acad. Sci. USA. 89, 7782–7785). Below are the experimental procedures for the assay of compounds.

All assays were performed using Chinese Hamster Ovary cells stably expressing the human dopamine transporter cDNA (hDAT cells). hDAT cells were distributed in 96-well plates and grown 3 to 4 days to confluency (~$10^5$ cells/well) in Ham's F12 medium containing 10% fetal calf serum. To facilitate comparisons, dopamine uptake and cocaine analogue binding were performed under identical conditions including assay buffers, temperature and time as detailed below.

[$^3$H]DOPAMINE UPTAKE

To assess [$^3$H]dopamine uptake, the hDAT cells were washed two times in Krebs-Ringer-HEPES buffer containing 100 µM ascorbic acid (KRH+) at room temperature. Cells were then incubated with 100 nM [$^3$H]dopamine (24.1 Ci/mmol; NEN) in KRH+ buffer for 6 minutes at room temperature. Co-incubation with 100 mM unlabeled (−) cocaine in parallel incubations allowed estimation of non-specific uptake. Uptake was terminated by five washes with ice-cold KRH+ and radioactivity was quantitated using a Packard TopLoad Scintillation Counter.

For uptake inhibition studies, cells were pre-incubated with the test compound for 2 hours in cell culture medium at 37° C. Subsequently, the hDAT cells were washed two times in KRH+ buffer at room temperature. The cells were then incubated with 100 nM [$^3$H]dopamine and test compound in KRH+ buffer at room temperature for 6 minutes. Binding was terminated and quantified as above. Data was analyzed and inhibition constants (Ki) were calculated using the Origin™ computer program by Microcal Software, Inc.

[$^3$H]CFT BINDING

To assess binding of the cocaine analogue (−)-2β-[$^3$H] carbomethoxy-3β-(4-fluorophenyl)tropane (CFT), the hDAT cells were washed two times in Krebs-Ringer-HEPES (KRH) buffer at room temperature. Cells were then incubated with 5 nM [$^3$H]CFT (87 Ci/mmol; NEN) in KRH buffer for 6 minutes at room temperature. Co-incubation with 100 µM unlabeled (−)cocaine in parallel incubations allowed estimation of nonspecific binding. Binding was terminated by five washes with ice-cold KRH and radioactivity was quantitated using a Packard TopLoad Scintillation Counter.

For binding inhibition studies, the hDAT cells were pre-incubated with test compound for 2 hours in cell culture medium at 37° C. Subsequently, the cells were washed three times in KRH buffer at room temperature. The cells were then incubated with 5 nM [$^3$H]CFT and test compound in KRH buffer at room temperature for 6 minutes. Binding was terminated and quantified as above. Data was analyzed and inhibition constants ($K_i$) were calculated using the Origin™ computer program by Microcal Software, Inc.

Utility and Administration

The compounds of the present invention can be used in the form of salts derived from inorganic or organic acids and bases. Included among such acid salts are the following: acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The compounds of the present invention can be administered to humans undergoing treatment for cocaine treatment or overdose, or for disease states and conditions characterized by abnormal dopaminergic neurotransmission. The compounds of the present invention can also be administered to mammals other than humans for treatment of various mammalian disease states and conditions characterized by abnormal dopaminergic neurotransmission.

The compounds of the present invention exhibiting uptake to binding ratios greater than that of cocaine, bind potently to the cocaine site on the dopamine transporter protein and have little or no effect on dopamine uptake. This activity is useful in the treatment of cocaine addiction and overdose.

The compounds of the present invention which bind at the cocaine site, but are not completely selective, may inhibit dopamine reuptake. This activity is useful in the treatment of disease states and conditions characterized by abnormal dopaminergic neurotransmission, including without limitation: Parkinson's disease, depression, attention deficit disorder (ADD), hypertension, congestive heart failure, acute and chronic renal failure, angina, hyperprolatenemia, psychoses, galactorrhea, menstrual disorders, sexual dysfunction, Huntington's chorea, and schizophrenia.

For these purposes, the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

To be effective therapeutically as central nervous system targets, the drug complex should readily penetrate the blood-brain barrier when peripherally administered. Compounds of this invention which cannot penetrate the blood-brain barrier can be effectively administered by an intraventricular route.

The compounds may be in the form of a sterile injectable preparation, for example as a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. Fatty acids such as oleic acid and its glyceride derivatives find use in the preparation of injectables, olive oil or castor oil, especially in their polyoxyethylated versions. These oil solutions or suspensions may also contain a long-chain alcohol diluent or dispersant.

The compounds may be administered orally in the form of capsules or tablets, for example, or as an aqueous suspension or solution. In the case of tablets or oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is optimally combined with emulsifying and suspending agents. If desired, certain sweetening and/or flavoring and/or coloring agents may be added.

The compounds of this invention may also be administered in the form of suppositories for rectal administration of the drug. These compositions can be prepared by mixing the drug with a suitable non-irritating excipient which is solid at room temperature but liquid at rectal temperature and therefore will melt in the rectum to release the drug. Such materials include cocoa butter, beeswax and polyethylene glycols.

The compounds of this invention may also be administered optically, especially when the conditions addressed for treatment involve areas or organs readily accessible by topical application, including neurological disorders of the eye, the skin, or the lower intestinal tract. Suitable topical formulations are readily prepared for each of these areas.

For ophthalmic use, the compounds can be formulated as micronized suspensions in isotonic, pH adjusted sterile saline, or, preferably, as solutions in isotonic, pH adjusted sterile saline, either with or without a preservative such as benzylalkonium chloride. Alternatively for the ophthalmic uses the compounds may be formulated in an ointment such as petrolatum.

For application topically to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal trace can be effected in a rectal suppository formulation (see above) or in a suitable enema formulation.

Dosage levels on the order of about 0.1 mg to about 10,000 mg of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

Pharmaceutical Compositions of the Invention

The present invention also relates to a pharmaceutical composition comprising (a) a therapeutically effective amount of a compound of formula

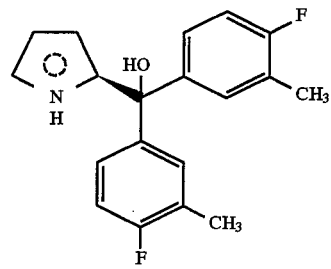

I or a pharmaceutically acceptable salt thereof, wherein
the compound is an R- or S-enantiomer;
the pyrrolidine ring is saturated or unsaturated;
$R_1$, $R_2$, $R_3$ and $R_4$ are independently selected from the group consisting of H, $C_1$–$C_6$ alkyl, hydroxy, carboxy, alkoxy and substituted $C_1$–$C_6$ alkyl group;
$R_1$, $R_2$, $R_3$ and $R_4$ are not all H; and
$Ar_1$ and $Ar_2$ are independently selected from the group consisting of an unsubstituted phenyl radical, a mono-substituted phenyl radical, and a multisubstituted phenyl radical, with substituents selected from the group consisting of halogen, $C_1$–$C_6$ alkyl, substituted alkyl, hydroxy, alkoxy, and carboxy; and (b) at least one of a pharmaceutically acceptable carrier, excipient or diluent.

In a preferred embodiment, the compound or the pharmaceutically acceptable salt thereof has an affinity for the cocaine binding site on a dopamine transporter protein (DAT). In another preferred embodiment, the compound or the pharmaceutically acceptable salt thereof permits a dopamine transporter protein (DAT) to maintain its function of accumulating dopamine. More preferably, the compound or the pharmaceutically acceptable salt thereof antagonizes cocaine's binding to a dopamine transporter protein (DAT) while permitting the DAT to maintain its function of accumulating dopamine.

In a further preferred embodiment, the compound or the pharmaceutically acceptable salt thereof has an uptake to binding ratio ($Ki_{uptake}/Ki_{binding}$) greater than that of cocaine. More preferably, the compound or the pharmaceutically acceptable salt thereof has an uptake to binding ratio ($Ki_{uptake}/Ki_{binding}$) of at least 2.

The above discussion relating to the utility and administration of the compounds of the present invention is also applicable to the pharmaceutical compositions of the present invention, and thus is hereby incorporated by reference.

Methods of Treating Disease States and Conditions Characterized by Abnormal Dopaminergic Neurotransmission Compounds which bind at the cocaine site and are not completely selective may inhibit dopamine reuptake. Compounds such as these may have utility in treating diseases in which low levels of dopamine have been implicated. The most notable disease states in this class are depression and Parkinson's disease.

Thus, the present invention also relates to methods of treating disease states and conditions characterized by abnormal dopaminergic neurotransmission, which comprises administering to a host suffering therefrom a therapeutically effective amount of a compound of the formula

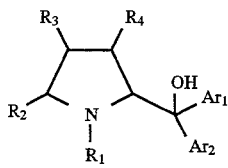

or a pharmaceutically acceptable salt thereof, wherein
the compound is an R- or S-enantiomer;
the pyrrolidine ring is saturated or unsaturated;
$R_1$, $R_2$, $R_3$ and $R_4$ are independently selected from the group consisting of H, $C_1$–$C_6$ alkyl, hydroxy, carboxy, alkoxy and substituted $C_1$–$C_6$ alkyl group;
$Ar_1$ and $Ar_2$ are independently selected from the group consisting of an unsubstituted phenyl radical, a mono-substituted phenyl radical, and a multisubstituted phenyl radical, with substituents selected from the group consisting of halogen, $C_1$–$C_6$ alkyl, substituted alkyl, hydroxy, alkoxy, and carboxy.

The treated disease states and conditions include but not limited to Parkinson's disease, depression, attention deficit disorder (ADD), hypertension, congestive heart failure, acute and chronic renal failure, angina, hyperprolatenemia, psychoses, galactorrhea, menstrual disorders, sexual dysfunction, Huntington's chorea, and schizophrenia. Preferably, the treated disease states and conditions are selected from the group consisting of Parkinson's disease, depression, and attention deficit disorder (ADD).

More preferably, the compound administered for treatment is selected from the group consisting of:
(S)-(–)-α,α-diphenyl-2-pyrrolidinemethanol;
(R)-(–)-α,α-diphenyl-2-pyrrolidinemethanol;
(S)-(–)-1-methyl-α,α-diphenyl-2-pyrrolidinemethanol;
(R)-(+)-1-methyl-α,α-diphenyl-2-pyrrolidinemethanol;
(S)-(–)-1-ethyl-α,α-diphenyl-2-pyrrolidinemethanol;
(R)-(+)-1-ethyl-α,α-diphenyl-2-pyrrolidinemethanol;
(S)-(–)-1-propyl-α,α-diphenyl-2-pyrrolidinemethanol;
(R)-(+)-1-propyl-α,α-diphenyl-2-pyrrolidinemethanol;
(S)-(–)-1-butyl-α,α-diphenyl-2-pyrrolidinemethanol;
(R)-(+)-1-butyl-α,α-diphenyl-2-pyrrolidinemethanol; and
(S)-α,α-Bis(3-methyl-4-fluorophenyl)-2-pyrrolidinemethanol.

Methods of Treating Cocaine Addiction and Overdose

Cocaine exerts its reinforcing properties by facilitating the action of the neurotransmitter dopamine in the mesolimbocortical pathways of the brain, a region responsible for the regulation of pleasure and reward. Cocaine does so by inhibiting the functioning of the dopamine transporter (DAT) protein. This inhibition results in excess levels of synaptic dopamine and enhanced dopaminergic transmission.

In 1992, two independent laboratories reported the molecular cloning of the human DAT. Subsequent site-directed mutagenesis studies employing the DAT clone demonstrated that dopamine uptake and cocaine binding occur at distinct sites on the transporter protein. This is significant because it means that drugs can be designed to specifically inhibit cocaine recognition by the DAT while permitting the transporter to maintain its function of accumulating dopamine. This selectivity is important because such a drug would block the physiological effects of cocaine while leaving normal dopamine transmission within the brain intact.

Accordingly, selective cocaine antagonists and mixed agonist/antagonists may have clinical utility in the treatment of cocaine addiction and overdose. Specifically, such compounds would exhibit high uptake to binding ratios ($Ki_{uptake}/Ki_{binding}$), which mean that the compounds would bind potently to the cocaine site on the dopamine transporter protein (expressed as $Ki_{binding}$) and have little or no effect on dopamine uptake (expressed as $Ki_{uptake}$). Stated in other terms, the compounds would antagonize cocaine's binding to the DAT while exhibiting minimal effects on transport function.

Thus, the present invention also relates to methods of treating cocaine addiction or overdose, which comprises administering to a host suffering therefrom a therapeutically effective amount of a compound of the formula

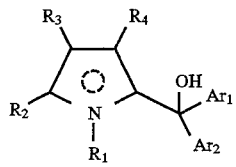

or a pharmaceutically acceptable salt thereof, wherein
the compound is an R- or S-enantiomer;
the pyrrolidine ring is saturated or unsaturated;
$R_1$, $R_2$, $R_3$ and $R_4$ are independently selected from the group consisting of H, $C_1$–$C_6$ alkyl, hydroxy, carboxy, alkoxy and substituted $C_1$–$C_6$ alkyl group;
$Ar_1$ and $Ar_2$ are independently selected from the group consisting of an unsubstituted phenyl radical, a mono-substituted phenyl radical, and a multisubstituted phenyl radical, with substituents selected from the group consisting of halogen, $C_1$–$C_6$ alkyl, substituted alkyl, hydroxy, alkoxy, and carboxy.

In a preferred embodiment, the compound administered for treating cocaine addiction or overdose is selected from the group consisting of:
(S)-(–)-α,α-diphenyl-2-pyrrolidinemethanol;
(R)-(–)-α,α-diphenyl-2-pyrrolidinemethanol;
(S)-(–)-1-methyl-α,α-diphenyl-2-pyrrolidinemethanol;
(R)-(+)-1-methyl-α,α-diphenyl-2-pyrrolidinemethanol;
(S)-(–)-1-ethyl-α,α-diphenyl-2-pyrrolidinemethanol;
(R)-(+)-1-ethyl-α,α-diphenyl-2-pyrrolidinemethanol;
(S)-(–)-1-propyl-α,α-diphenyl-2-pyrrolidinemethanol;
(R)-(+)-1-propyl-α,α-diphenyl-2-pyrrolidinemethanol;
(S)-(–)-1-butyl-α,α-diphenyl-2-pyrrolidinemethanol;
(R)-(+)-1-butyl-α,α-diphenyl-2-pyrrolidinemethanol; and
(S)-α,α-Bis(3-methyl-4-fluorophenyl)-2-pyrrolidinemethanol.

All publications and patents identified above are hereby incorporated by reference.

The invention being thus described, it will be obvious that the same may be varied in many ways. Such variations are not to be regarded as a departure from the spirit and scope of the invention and all such modifications are intended to be included within the scope of the following claims.

What is claimed is:

1. A compound of the formula

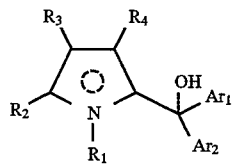

or a pharmaceutically acceptable salt thereof, wherein
the compound is an R- or S-enantiomer;
the pyrrolidine ring is saturated or unsaturated;
$R_1$, $R_2$, $R_3$ and $R_4$ are independently selected from the group consisting of H, $C_1-C_6$ alkyl, hydroxy, carboxy, alkoxy and substituted $C_1-C_6$ alkyl group, provided that $R_1$, $R_2$, $R_3$ and $R_4$ are not all H; and
$Ar_1$ and $Ar_2$ are independently selected from the group consisting of 4-fluorophenyl, 4-chlorophenyl, and 3-methyl-4-fluorophenyl.

2. The compound of claim 1, wherein $R_1$ is selected from the group consisting of methyl, ethyl, propyl and butyl.

3. A pharmaceutical composition comprising:
(a) a therapeutically effective amount of a compound of formula

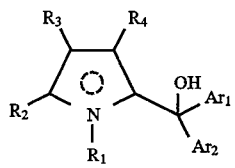

or a pharmaceutically acceptable salt thereof, wherein the compound is an R- or S-enantiomer; the pyrrolidine ring is saturated or unsaturated; $R_1$, $R_2$, $R_3$, and $R_4$ are independently selected from the group consisting of H, $C_1-C_6$ alkyl, hydroxy, carboxy, alkoxy and substituted $C_1-C_6$ alkyl group, provided that $R_1$, $R_2$, $R_3$, and $R_4$ are not all H; and
$Ar_1$ and $Ar_2$ are independently selected from the group consisting of 4-fluorophenyl, 4-chlorophenyl, and 3-methyl-4-fluorophenyl.

4. The pharmaceutical composition of claim 3, wherein the compound or the pharmaceutically acceptable salt thereof has an affinity for the cocaine binding site on a dopamine transporter protein (DAT).

5. The pharmaceutical composition of claim 3, wherein the compound or the pharmaceutically acceptable salt thereof permits a dopamine transporter protein (DAT) to maintain its function of accumulating dopamine.

6. The pharmaceutical composition of claim 3, wherein the compound or the pharmaceutically acceptable salt thereof antagonizes cocaine's binding to a dopamine transporter protein (DAT) while permitting the DAT to maintain its function of accumulating dopamine.

7. The pharmaceutical composition of claim 3, which has an uptake to binding ratio ($Ki_{uptake}/Ki_{binding}$) greater than that of cocaine.

8. The pharmaceutical composition of claim 3, which has an uptake to binding ratio ($Ki_{uptake}/Ki_{binding}$) of at least 2.

9. A method of treating a disease state or condition characterized by abnormal dopaminergic neurotransmission, which comprises administering to a host suffering therefrom a therapeutically effective amount of a compound having the formula

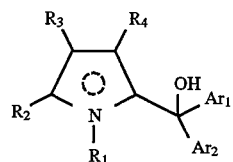

or a pharmaceutically acceptable salt thereof, wherein
the compound is an R- or S-enantiomer;
the pyrrolidine ring is saturated or unsaturated;
$R_1$, $R_2$, $R_3$ and $R_4$ are independently selected from the group consisting of H, $C_1-C_6$ alkyl, hydroxy, carboxy, alkoxy and substituted $C_1-C_6$ alkyl group; and
$Ar_1$ and $Ar_2$ are independently selected from the group consisting of an unsubstituted phenyl radical, a mono-substituted phenyl radical, and a multisubstituted phenyl radical, with substituents selected from the group consisting of halogen, $C_1-C_6$ alkyl, substituted alkyl, hydroxy, alkoxy, and carboxy.

10. The method of claim 9, wherein the disease state or condition is Parkinson's disease.

11. The method of claim 9, wherein the disease state or condition is depression.

12. The method of claim 9, wherein the disease state or condition is attention deficit disorder (ADD).

13. The method of claim 9, wherein the compound is selected from the group consisting of:
(S)-(−)-α,α-diphenyl-2-pyrrolidinemethanol;
(R)-(−)-α,α-diphenyl-2-pyrrolidinemethanol;
(S)-(−)-1-methyl-α,α-diphenyl-2-pyrrolidinemethanol;
(R)-(+)-1-methyl-α,α-diphenyl-2-pyrrolidinemethanol;
(S)-(−)-1-ethyl-α,α-diphenyl-2-pyrrolidinemethanol;
(R)-(+)-1-ethyl-α,α-diphenyl-2-pyrrolidinemethanol;
(S)-(−)-1-propyl-α,α-diphenyl-2-pyrrolidinemethanol;
(R)-(+)-1-propyl-α,α-diphenyl-2-pyrrolidinemethanol;
(S)-(−)-1-butyl-α,α-diphenyl-2-pyrrolidinemethanol;
(R)-(+)-1-butyl-α,α-diphenyl-2-pyrrolidinemethanol; and
(S)-α,α-Bis(3-methyl-4-fluorophenyl)-2-pyrrolidinemethanol.

14. A method of treating cocaine addiction or overdose, which comprises administering to a host suffering therefrom a therapeutically effective amount of a compound having the formula

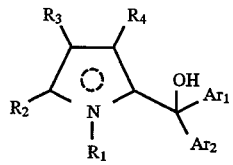

or a pharmaceutically acceptable salt thereof, wherein
the compound is an R- or S-enantiomer;
the pyrrolidine ring is saturated or unsaturated;
$R_1$, $R_2$, $R_3$ and $R_4$ are independently selected from the group consisting of H, $C_1-C_6$ alkyl, hydroxy, carboxy, alkoxy and substituted $C_1-C_6$ alkyl group;

Ar₁ and Ar₂ are independently selected from the group consisting of an unsubstituted phenyl radical, a monosubstituted phenyl radical, and a multisubstituted phenyl radical, with substituents selected from the group consisting of halogen, $C_1$–$C_6$ alkyl, substituted alkyl, hydroxy, alkoxy, and carboxy.

15. The method of claim 14, wherein the compound is selected from the group consisting of:

(S)-(−)-α,α-diphenyl-2-pyrrolidinemethanol;
(R)-(−)-α,α-diphenyl-2-pyrrolidinemethanol;
(S)-(−)-1-methyl-α,α-diphenyl-2-pyrrolidinemethanol;
(R)-(+)-1-methyl-α,α-diphenyl-2-pyrrolidinemethanol;
(S)-(−)-1-ethyl-α,α-diphenyl-2-pyrrolidinemethanol;
(R)-(+)-1-ethyl-α,α-diphenyl-2-pyrrolidinemethanol;
(S)-(−)-1-propyl-α,α-diphenyl-2-pyrrolidinemethanol;
(R)-(+)-1-propyl-α,α-diphenyl-2-pyrrolidinemethanol;
(S)-(−)-1-butyl-α,α-diphenyl-2-pyrrolidinemethanol;
(R)-(+)-1-butyl-α,α-diphenyl-2-pyrrolidinemethanol; and
(S)-α,α-Bis(3-methyl-4-fluorophenyl)-2-pyrrolidinemethanol.

16. A compound of the formula

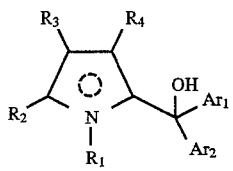

or a pharmaceutically acceptable salt thereof, wherein
the compound is an R- or S-enantiomer;
the pyrrolidine ring is saturated or unsaturated;
$R_1$, $R_2$, $R_3$ and $R_4$ are independently selected from the group consisting of H, $C_1$–$C_6$ alkyl, hydroxy, carboxy, alkoxy and substituted $C_1$–$C_6$ alkyl group; and
Ar₁ and Ar₂ are independently a phenyl radical substituted with a fluorine, bromine or iodine, and at least one other substituent selected from the group consisting of $C_1$–$C_6$ alkyl, substituted alkyl, hydroxy, alkoxy, and carboxy.

17. The compound of claim 16 which is (S)-α,α-Bis(3-methyl-4-fluorophenyl)-2-pyrrolidinemethanol.

* * * * *